United States Patent
Arissian et al.

(10) Patent No.: US 9,859,677 B1
(45) Date of Patent: Jan. 2, 2018

(54) NESTED FREQUENCY COMBS

(71) Applicant: STC.UNM, Albuquerque, NM (US)

(72) Inventors: Ladan Arissian, Albuquerque, NM (US); Jean-Claude Diels, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 0 days.

(21) Appl. No.: 15/488,088

(22) Filed: Apr. 14, 2017

Related U.S. Application Data

(62) Division of application No. 14/537,574, filed on Nov. 10, 2014, now Pat. No. 9,653,877.

(60) Provisional application No. 61/902,063, filed on Nov. 8, 2013.

(51) Int. Cl.
*G01N 21/41* (2006.01)
*H01S 3/11* (2006.01)
*H01S 3/0957* (2006.01)
*H01S 3/106* (2006.01)

(52) U.S. Cl.
CPC ........ *H01S 3/1112* (2013.01); *G01N 21/4133* (2013.01); *H01S 3/0957* (2013.01); *H01S 3/1062* (2013.01); *G01N 2201/06113* (2013.01)

(58) Field of Classification Search
CPC .. G01N 21/41; G01N 21/4133; G01N 21/431; G01N 21/43; G01N 21/552
USPC ........................................................ 356/128
See application file for complete search history.

(56) References Cited

U.S. PATENT DOCUMENTS

| | | |
|---|---|---|
| 8,929,408 B1 | 1/2015 | Diels et al. |
| 9,653,877 B1 | 5/2017 | Arissian et al. |
| 2005/0190805 A1 | 9/2005 | Scripsick et al. |
| 2011/0043815 A1 | 2/2011 | Giaccari et al. |
| 2011/0110388 A1 | 5/2011 | Baroni et al. |
| 2015/0198437 A1 | 7/2015 | Wolf et al. |

OTHER PUBLICATIONS

"U.S. Appl. No. 14/537,574, 312 Amendment filed Apr. 6, 2017 in response to the Notice of Allowance dated Jan. 17, 2017", 8 pgs.
"U.S. Appl. No. 14/537,574, Non Final Office Action dated Sep. 6, 2016", 15 pgs.
"U.S. Appl. No. 14/537,574, Notice of Allowance dated Jan. 17, 2017", 7 pgs.
"U.S. Appl. No. 14/537,574, PTO Response to Rule 312 Communication dated Apr. 12, 2017", 2 pgs.
"U.S. Appl. No. 14/537,574, Response filed Jul. 29, 2016 to Restriction Requirement dated Jun. 1, 2016", 6 pgs.
"U.S. Appl. No. 14/537,574, Response filed Dec. 9, 2016 to Non-Final Office Action dated Sep. 6, 2016", 12 pgs.
"U.S. Appl. No. 14/537,574, Restriction Requirement dated Jun. 1, 2016", 6 pgs.

(Continued)

*Primary Examiner* — Tarifur Chowdhury
*Assistant Examiner* — Md M Rahman
(74) *Attorney, Agent, or Firm* — Schwegman Lundberg & Woessner, P.A.

(57) ABSTRACT

Apparatus, systems, and methods of generating multi combs can be used in a variety of applications. In various embodiments, a passive resonator can be disposed in the laser cavity of a mode-locked laser to generate a nested frequency comb. The passive resonator can be a sample under investigation, where a characteristic of the sample is determined using the generated nested frequency comb. Additional apparatus, systems, and methods are disclosed.

8 Claims, 16 Drawing Sheets

(56) References Cited

OTHER PUBLICATIONS

Arissian, Ladan, et al., "Investigation of carrier to envelope phase and repetition rate: fingerprints of mode-locked laser cavities", *Journal of Physics B: Atomic, Molecular and Optical Physics 42*, 183001, (2009), 1-25.

Arrissian, Ladan, et al., "Repetition rate spectroscopy of the dark line resonance in rubidium", *Optics Communications*, 264, (2006), 169-173.

Hecht, Adam, et al., "A New Method of Radiation Sensing and Analysis", (Abstract), *54th Annual Meeting of the Institute of Nuclear Materials Management (INMM 2013)*, (2013), 2 pgs.

Masuda, Koji, et al., "Intracavity coherent interaction of mode-locked pulse train with resonany medium", *Dissertation, the University of New Mexico*, (Jul. 2014), 201 pgs.

NESTED FREQUENCY COMBS

RELATED APPLICATION

This application is a divisional application of U.S. patent application Ser. No. 14/537,574, filed 10 Nov. 2014, which claims priority under 35 U.S.C. 119(e) from U.S. Provisional Application Ser. No. 61/902,063, filed 8 Nov. 2013, which applications are incorporated herein by reference in their entirety.

FIELD OF THE INVENTION

The invention relates generally to frequency combs and to systems and devices for the generation and/or use of the same.

BACKGROUND

An optical frequency comb is an optical spectrum of equidistant lines. The use of frequency combs as a tool may depend on the spacing between teeth (lines) of the comb. Mode-locked lasers can provide accurate frequency combs. A mode-locked laser produces a stream of identical pulses, which can have a duration of only several femtoseconds, at a repetition rate typically in the range of 70 to 150 MHz. In the frequency domain, the laser output consists of a frequency comb having equidistant lines. Because these lines are exactly equally spaced, this frequency comb can be used as a ruler for optical frequencies. Frequency combs may provide enhancements in other areas of measurement.

BRIEF DESCRIPTION OF THE FIGURES

Embodiments of the invention are illustrated by way of example and not limitation in the figures of the accompanying drawings in which.

DESCRIPTION

Figure 1:
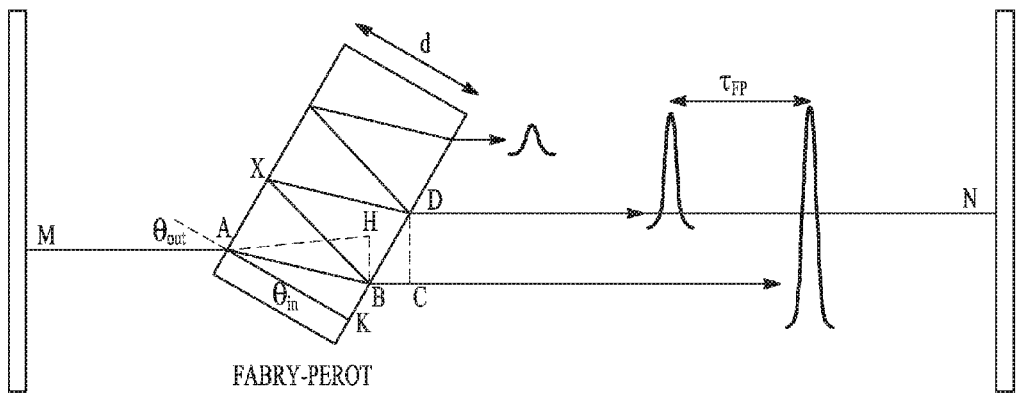
FIG. 1 is a sketch of transmission through a Fabry Perot structure inserted in a cavity.

The following detailed description refers to the accompanying drawings that show, by way of illustration and not limitation, various example embodiments of the invention. These embodiments are described in sufficient detail to enable those skilled in the art to practice these and other embodiments. Other embodiments may be utilized, and structural, logical, and electrical changes may be made to these embodiments. The various embodiments are not necessarily mutually exclusive, as some embodiments can be combined with one or more other embodiments to form new embodiments. The following detailed description is, therefore, not to be taken in a limiting sense.

Output of a laser cavity represents properties of its medium. In a single frequency comb, the group and phase index of the cavity defines the position and spacing between frequencies. For the case of nested cavity, a high frequency comb is generated from a Fabry Perot etalon that is inserted in a cavity. The frequency comb of the Fabry Perot etalon inherits the linewidth of the laser cavity without involving complications of a gain medium. Using these nested cavities, the index of refraction of the Fabry Perot etalon can be measured with ultimate precision by measuring the high frequency RF (Fabry Perot etalon) and low frequency RF (laser repetition rate). Performing cavity scans by a) tilting the angle of Fabry-Perot and/or b) scanning of cavity length enhances the resolution in the index of refraction measurement.

Simple etalons inserted in a laser cavity of a laser can be used to tune the wavelength of the laser. Inserting such an element inside a mode-locked laser can lead to a frequency comb with counter-intuitive features. Instead of a decaying sequence of pulses, the etalon produces a symmetric bunch of pulses, at a repetition rate in the GHz range, that can be fine tuned with the laser cavity length. The wavelength of the laser—as in the continuous wave (cw) case—can be tuned with the angle of the etalon. However, in the case of the mode-locked laser, the high frequency (HF) of the Fabry Perot etalon and low frequency (LF) components of the repetition rate are both modified with the angle of incidence. As a result, a nested comb can be generated on a mode-locked comb. For example, a nested comb of 6-10 GHz can be generated on a mode-locked comb of around 100 MHz in a meter long Ti:Sapphire laser.

This unique design combines the narrow line width of the laser cavity, which is a Fabry Perot (FP) structure with gain, with the accessible Fabry-Perot sensor as an etalon, where the sensor can be arranged as a workpiece. For example, the workpiece can be a piece of glass or other transparent material arranged as a FP etalon. Tuning parameters and coupling of the nested frequency comb can be adjusted for application in measurement of refractive index. Examples of using methods discussed herein includes, but is not limited to, measuring the change of the index of refraction of a sample as a function of a stimulus applied to the sample. For example, the change of index was measured and recorded for a 1.4 cm etalon of $CaF_2$ that had been exposed with PuBe with 6 curie (Ci) of radiation.

In various embodiments, architectures with one or more passive etalons inserted in a mode-locked laser cavity can provide precise and selective radiation sensing. Methods using such architectures can be implemented in, but are not limited to, applications detecting neutrons and/or detecting and discerning gamma (γ) rays from neutrons. Architectures with one or more passive etalons inserted in a mode-locked laser cavity can provide a mechanism to sense changes of indices of refraction with utmost sensitivity. These architectures and methods can be utilized to investigate the immediate and long term impact of different radiation on the index of refraction and other optical properties of materials, and use data collected to identify different radiation. The extent of radiation induced refractive index change in optical materials can be determined as a function of the amount of radiation irradiating the respective optical materials. In addition to radiation exposure history determination, these architectures and method may be utilized to control materials properties with great precision to create novel materials and devices having advanced functionality.

Radiation damage from neutrons is dominated by atomic lattice displacements and damage from gamma rays is dominated by electron displacements. Electron displacements cause color centers that can be detected through discrete absorption lines. Sensor elements can include ionic crystals and semiconductors. In ionic solids, such as CaF, LiF, NaCl, NaF, neutrons displace atoms by recoils of primary knock-out atoms (PKA), which then displace many more secondary ions. As long as the energy transferred in a neutron collision is higher than the displacement energy (typically tens of eV) then a PKA may be released, causing a cascade of displacement. As an example, it has been reported that a 0.5 MeV neutron on iron may cause 350 displacements from a single PKA. As the neutron scatters down several hundred times in the material, each time producing a PKA, the total lattice displacement damage due to a single neutron can be tremendous. The best selection of two crystals may be realized for differential measurement for a dual neutron-gamma sensor.

Displacement damage due to neutrons is of course a function of displacement energy for that material, but it is also tied to the damage efficiency for the recoiling PKA. For the same incident neutron energy, lighter ions recoil with more energy than heavier ions, which should produce more atomic displacements, but they also share a larger portion of their energy with electrons, producing color centers. For small crystals (mm scale) the neutron mean free path at fission neutron energies reduces the probability of multiple scatters in the material, reducing the energy transfer to a single neutron collision, so for small samples lighter ion crystals should show more total displacements. The measurement configuration can be applied to materials composed of lower mass ions and of higher mass ions to examine their different response. LiF appears to be a good light mass candidate, since it has excellent optical qualities over a very large bandwidth. Li neutron absorption can also aid in energy absorption.

In contrast to neutron induced damage, gamma ray damage is strongly dominated by production of color centers due to the interactions primarily with electrons, with very little atomic displacement due to subsequent fast electron collisions. Gamma-ray interactions are dependent on proton number (Z), and as Z increases with atomic mass (A), a lower atom mass crystal will reduce this effect. Color centers lasers have a very high cross section of absorption and emission. The color center formed ($F_2$, $F_2^+$, $F_2^-$, and $F_3^+$) and its lifetime depends on the temperature of the sample, the energy and nature of the irradiating radiation (g-ray, electron beam, x-ray, UV, or ionic bombardment). The response of the same LiF sample to gamma rays can be compared with neutron response, as well as lead phosphate glasses in which the absorption line shifts to lower energy with high gamma radiation. Traditionally, the color centers are monitored with measurement of absorption lines. In this method, the index of refraction which follows the absorption through Kramers Kronig relation can be measured.

Response to radiation fields such as fission spectrum neutrons and gamma/x-rays in the low energy (<100 keV) and higher ($^{60}Co$) energy regimes can be studied using methods related to nested frequency combs. Since materials respond differently to different radiations based on A and Z, the optical response for low atom and high ion mass crystals can be characterized.

In various embodiments, architectures and techniques can be implemented with a mode-locked laser cavity. For example, a nested comb can be generated to characterize materials. The generation of nested comb can be realized using a passive resonator, such as a Fabry Perot etalon (FPE), inserted in a mode-locked laser cavity. The gain dynamics inside the laser can result in the generation of two nested frequency combs. The resonant condition couples these frequencies. This coupling provides a unique environment to measure phase and group index of the laser cavity and the etalon. The absolute optical frequency can be determined by the phase index in the etalon and phase index in the laser cavity. The high RF (radio frequency) frequency is defined by the optical length of the etalon and the group index of the cavity. The coupling between low RF (repetition rate) and high RF frequency determines the group and phase index of refraction. Scanning the cavity length of the laser resonator and angle tuning of the etalon provides higher precision to the index measurement.

The optical frequency of the laser cavity is set by the Fabry Perot structure inserted in the laser cavity. This resonance set is for the central frequency lasing in the laser cavity, in other words, it basically has nothing to do with pulse operation. In order to have a constructive interference between the two passages in a small Fabry Perot structure with thickness, d, and index of refraction, n, at normal incidence, the phase difference, $\Phi_{FP}$, between the two passage should be a multiple of $2\pi$, $$\Phi_{FP} = 2kdn = 2N\pi. \quad (1)$$

As the Fabry Perot structure is rotated, a change in phase is induced, but the resonance should persist and the phase has to stay multiple of $2\pi$ $$\Delta\Phi_{FP} = 2kdn \cos(\theta) = 0 \text{ or } 2\pi \text{ or } 4\pi. \quad (2)$$

As the internal angle of Fabry Perot structure changes for the range of 0.01 radian the optical frequency undergoes 3 oscillations with amplitude of Fabry-Perot frequency. The absolute optical frequency can only change by maximum of $v_{FP}$. One can confirm this frequency change by looking at the fluorescence of D1 line of rubidium, where three resonances can be observed.

The optical frequency is set by the resonance in the Fabry Perot structure. This effect can be examined and compared with a Fabry Perot structure outside a laser cavity. When placed outside the cavity, the phase change due to rotation of the Fabry-Perot can be converted to time delay between the pulses, inside the laser it is converted to change in optical frequency. When inserted in the cavity the rotation of the Fabry Perot structure does not change the timing between the pulses.

In a laser cavity of a mode-locked laser, the generated signal deals with pulses not a continuous wave. The Fabry-Perot structure is a slave passive cavity inside a laser cavity with gain. There is an offset frequency between optical frequency and Fabry-Perot frequency associated to the bunch generated. A passive cavity has a dispersion resulting to unequally spaced modes in frequency. Insertion of the FP inside a laser cavity results in soliton solution. The modes of the FP cavity can now be equally spaced. This comb is a comb with zero offset frequency because there is no gain mechanism to impose a phase shift between carriers.

In order to have the same carrier to envelope phase for the picosecond pulses, there is a minute change in the group velocity of the picosecond pulses; note that this change in time is at most only a fraction of the light period. For a 2 picosecond pulse, a change of quarter light period is $\Delta\tau_{FP} = 2.7/4 = 0.6$.

$$(\Delta\tau_{FP}/\tau_{FWHM}) = (\Delta v_{FP}/v_{FWHM}) \quad (3)$$

So the group velocity of the Fabry Perot frequency is only 0.6 fs/148 ps or 27 kHz. The change of phase mentioned in the previous part in the frequency of Fabry-Perot pulse was not seen.

As the frequency in the cavity is changed, the total phase in the cavity modifies. This modification will result in the total phase delay being compensated with the group delay in order to keep the offset frequency between optical frequency and repetition rate constant. In other words, the total phase experience of the phase frequency changes not by changing length, only by changing frequency. One can say that this even happens in a laser cavity with birefringence, but in this case, the optical periods are not forced by a Fabry-Perot structure and there is no change in the gain mechanism while rotating a Fabry-Perot structure. The total phase experience is kL in half cavity length. So the change of frequency initiated from the FP resonance imposes a phase change on the phase of the laser cavity. This phase change is proportional to $2\Delta k$ for one passage through the Fabry-Perot structure.

Because of the geometry of the problem, by having a FP structure inside the laser cavity, the total phase change with be $\Delta\Phi = 2 \times 2\Delta kL$ in half cavity round trip. This will result in $$(\Delta v_{rep}/v_{rep}) = (4 \times \Delta v_{opt})/v_{opt} = 4 \times 6 \times 10^{-5}, \quad (4)$$

which will result in 37 kHz change in the repetition (rep) rate. Note that this corresponds to only one picosecond change in time, less than a pulse width.

In dealing with mode-locked lasers, the traditional approach is to make a Fourier transform of identical pulses appearing at each cavity round trip. For the situation disclosed herein, a bunch of pulses is encountered at each cavity round trip. Consider the spectrum of this train by considering $$E(\Omega) = \int E(t) e^{-i\Omega t} dt \quad (5)$$

Since a shift in delta function is just a phase in frequency domain $$\delta(x - x_0) e^{-2\pi i k x} dx = e^{-2\pi i k x} \quad (6)$$

the series of delta functions in time domain can be seen in freq domain as $$E(\Omega) = \int \delta(t - N_{FP}\tau_{FP}) \delta(t - N_{trt}\tau_{RT}) \tilde{E}_0 e(-i\omega t) dt \quad (7)$$

since the pulses exist only for $t = N_{FP}\tau_{FP} + N_{trt}\tau_{RT}$. Note that $N_{trt}$ goes from "0" to infinity while $N_{FP}$ goes from −5 to 5.

$$E[\Omega] = \sum_{N_{trt}=0}^{\infty} \sum_{N_{FP}=-5}^{N_{FP}=5''} \quad (8)$$

$$= \sum_{N_{trt}=0}^{\infty} \tilde{E}_0 e^{-i\omega N_{trt}\tau_{RT}} [1 + 2\cos(\omega\tau_{RT}) + 2\cos(2\omega\tau_{RT}) +$$

$$2\cos(3\omega\tau_{RT}) + 2\cos(4\omega\tau_{RT}) + 2\cos(5\omega\tau_{RT})]$$

This Fourier transform does not provide any insight to the relation between optical frequency and high and low (repetition rate) RF frequency. If the high RF frequency is not an integer multiplication of the repetition rate, then in order to form a pulse train in the cavity the comb structure is discontinuous. This discontinuity is a matter of perception. One can say that the high RF frequency is not built upon the mode-locked comb structure, the new comb structure is shifted to a high frequency comb of the order of 10 GHz with sidebands of repetition rate that covers the bandwidth of a bunch (for a nanosecond bunch the spectrum bandwidth around each high frequency is 1 GHz). The Fourier transform shows for a given set of frequencies in the cavity what is the proper structure of a frequency comb and pulse train in time domain, without justifying the relation between those frequencies.

Consider the distances that light travels inside a Fabry Perot structure and in a laser cavity with physical dimension MN=L, as shown in FIG. 1.

$$AK = d \quad (9)$$

$$BXD = \frac{2d}{\cos\theta_{in}}$$

$$BC = 2d\tan\theta_{in}\sin\theta_{out}$$

$$\frac{AH}{AB} = \cos(\theta_{out} - \theta_{in})$$

$$AH = \frac{d\cos(\theta_{out} - \theta_{in})}{\cos\theta_{in}}$$

$$L = MA + AH + BC + DN$$

So far, physical distances have been considered and not the optical ones. The index of refraction, in terms of a phase index, $n_p$, arise from the Snell's law $$n_p \sin\theta_{in} = \sin\theta_{out} \quad (10)$$

The phase difference between the two passages in the Fabry-Perot is $$\Delta\Phi = 2k_0(n_p BXD - BC) = 2k_0 n_p d \cos\theta_{in} \quad (11)$$

Figure 2:
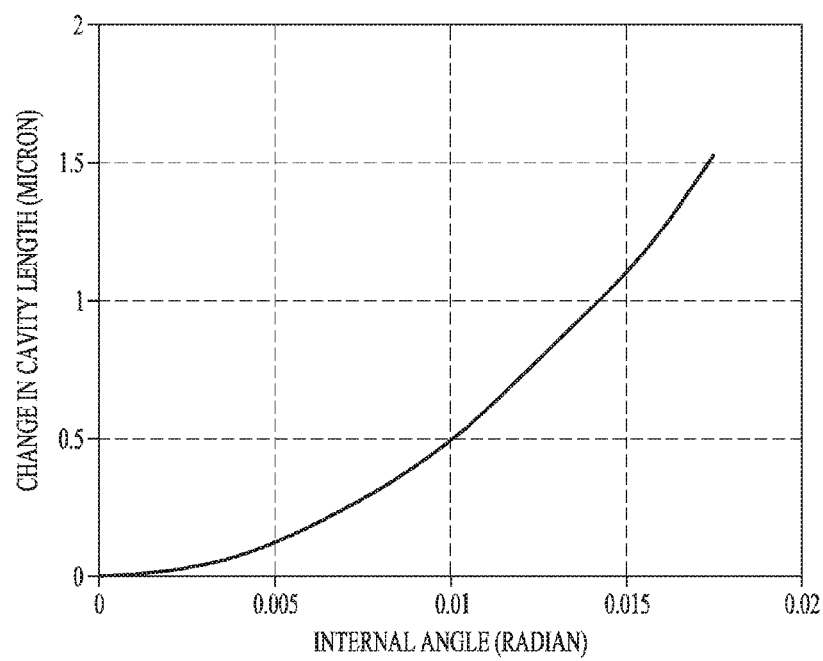
FIG. 2 illustrates the change in cavity length with internal angle of a Fabry Perot structure.
Figure 3:
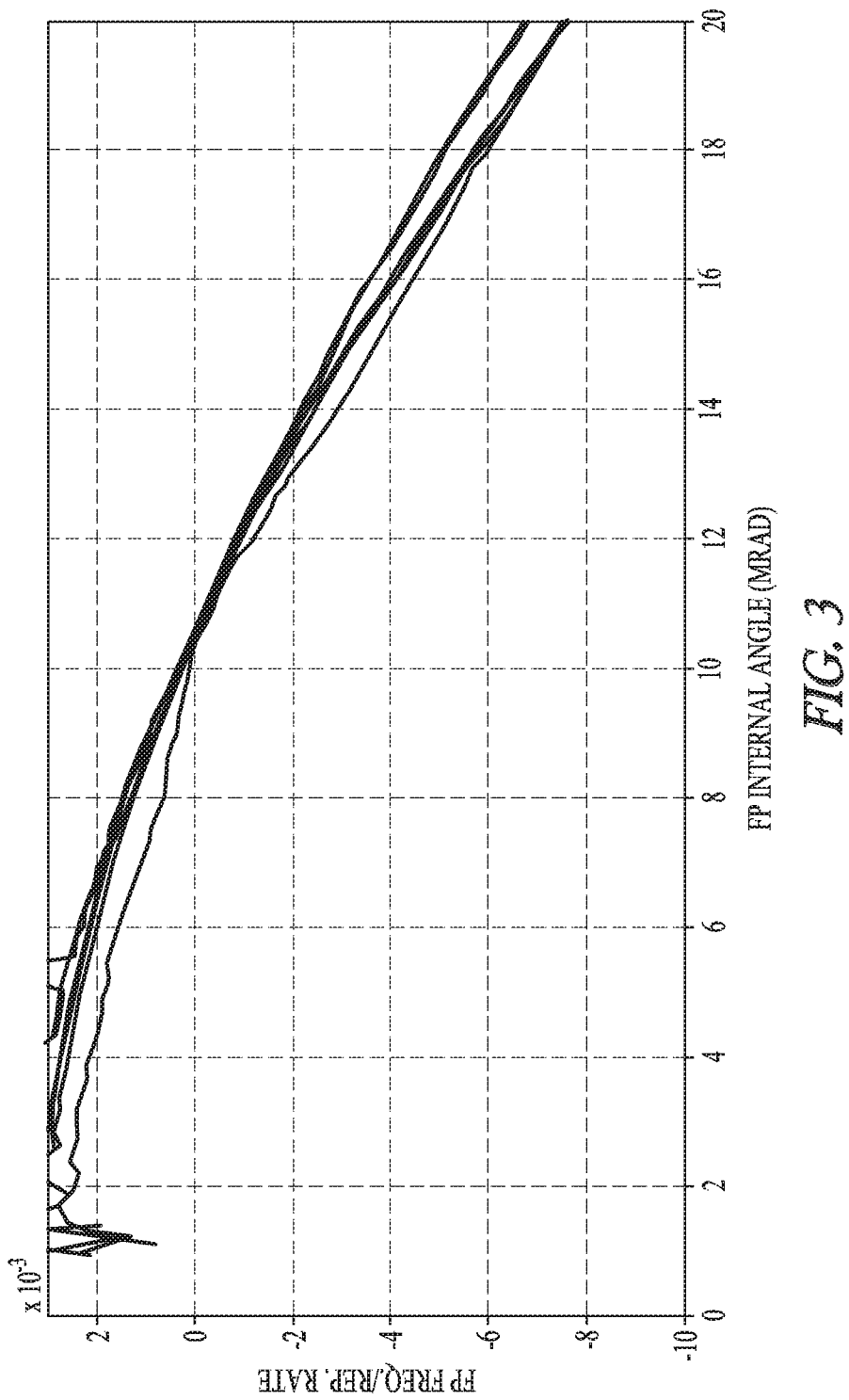
FIG. 3 shows ratio of the Fabry Perot frequency to repetition rate as a function of the Fabry Perot angle.

This is a very non trivial result; it states that the phase difference between multiple reflections reduces as the glass is rotated away from the normal incidence. The single passage though the glass, $AB = d/\cos\theta_{in}$, however increases with θ, but the difference between one bounce and two bounces is reduced. FIG. 2 shows the change of cavity length with $\theta_{in}$. FIG. 3 shows ratio of the Fabry Perot frequency to repetition rate as a function of the Fabry Perot angle for a number of samples.

As had been confirmed in dark line measurements, the central optical frequency can be tuned by rotating the Fabry Perot internal angle $$2\omega_0 d n_{p-FP} \cos\theta = 2N_{FP}\pi \quad (12)$$

The pulse period, however is defined with a group index $$\tau_{FP} = (2d n_{g-FP} \cos\theta)/c, \quad (13)$$

and the cavity pulse period by $$\tau_{RT} = (2 L n_{g-c})/c, \quad (14)$$

Since the optical frequency $\omega_0$ must be resonant simultaneously with the Fabry Perot and the laser cavity, the following is obtained $$\frac{2\omega_0 L n_{p-c}}{c} = 2N_c\pi \quad (15)$$

$$\frac{2\omega_0 d n_{p-FP}\cos\theta}{c} = 2N_{FP}\pi. \quad (16)$$

as a result $$\frac{L n_{p-c}}{d n_{p-FP}\cos\theta} = \frac{N_c}{N_{FP}}, 1 = 2 \quad (17)$$

which is not necessarily an integer. Here one should remember that the Fabry-Perot transmission linewidth is much broader that the laser cavity and further apart in frequency. The optical frequency of the cavity is defined by the Fabry-Perot large spacing and its precise value is set by the sharper teeth of the cavity. The high RF is an existing frequency in a cavity just like the optical frequency and needs to be resonant with the cavity as well. One can replace the values $$\nu_{FP} = \frac{c}{2d\cos\theta n_{gFP}} \text{ and } \nu_{RT} = \frac{c}{2L n_{gc}}$$

and reach to the resonant condition that locks the high RF with low (repetition rate) RF frequency.

$$\frac{\nu_{RT} n_{g-FP} n_{p-c}}{\nu_{FP} n_{p_c} n_{p-FP}} = \frac{N_c}{N_{FP}}, \quad (18)$$

The coupling of the HF of an FPE and the LF of the repetition rate of the laser can be exploited for a high resolution measurement of a small change in the index of refraction of the FPE. The coupling of HF and LF arises because of the simultaneous resonance of the two cavities. The ratio of HF to LF as given as $$(f_{FP}/f_{rep}) = (n_{gL} n_{pFP} N_L)(n_{gFP} n_{pL} N_{FP}) \quad (19)$$

must be very close to an integer in order for the HF pulse train to form. The first term of the right hand side is a ratio of the group index of the laser cavity to that of the FPE, which are predominantly determined by pulse dynamics due to gain-loss balance and to the condition for the build-up of the HF pulse train. The third term is a ratio of integers that are determined by the physical dimension of the cavities, L and d. Therefore, the first and the third terms remain the same as long as the cavity conditions, including pump power, alignment, and cavity length, are unchanged. Now, the second term is a ratio of the phase index of refraction of the FPE to that of the laser cavity, which are unique physical quantities to the material of the object. Assuming the cavity conditions are unchanged, if there is a change in the index of refraction of FPE, it will be reflected to the ratio of IV to LF.

It is known that bombardment of high-energy particles, such as neutrons, can damage the lattice structure of crystals. Changes in the lattice structure (dislocations) should impact the index of refraction of the material. For trial experiments, several samples of $CaF_2$ were be irradiated by a neutron beam with different dosage.

Figure 4A:
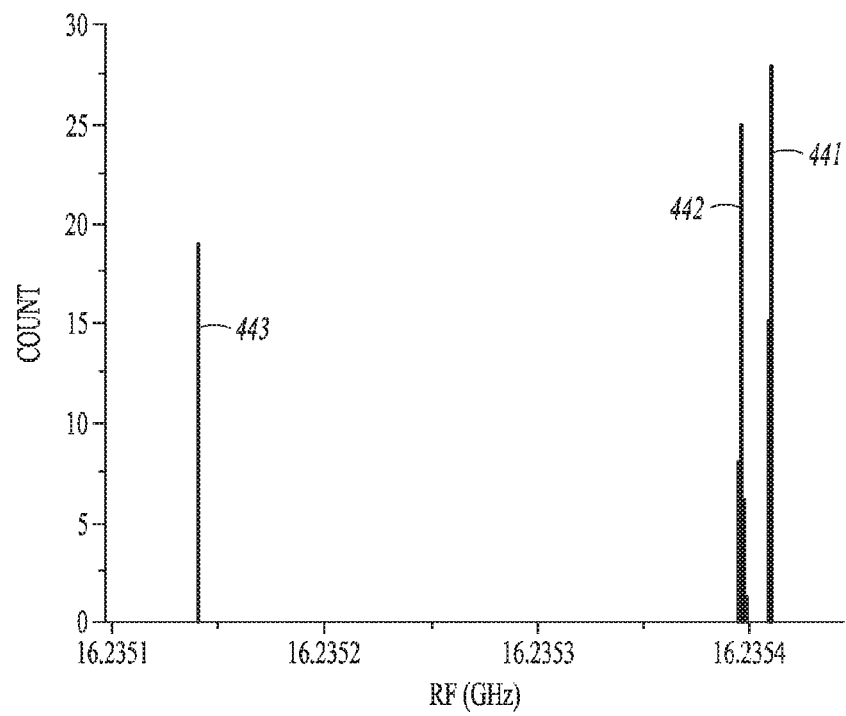
FIG. 4A shows measurements of the high frequency mode of a Fabry Perot etalon for three samples, measured with a 26 GHz spectrum analyzer over 1 min.
Figure 4B:
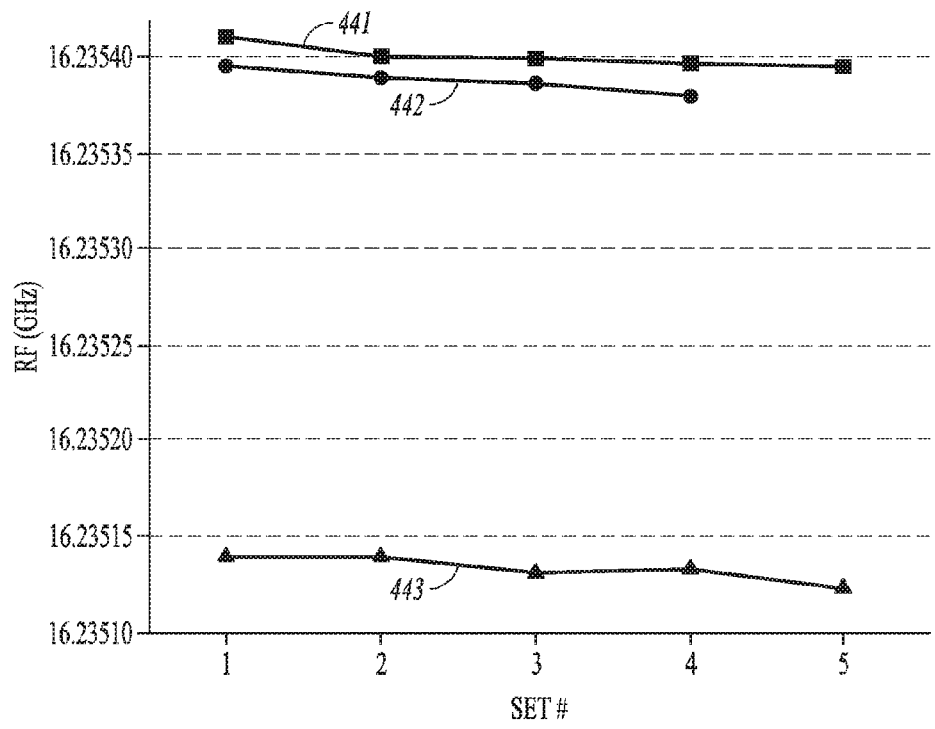
FIG. 4B shows five measurements of the high frequency mode of a Fabry Perot etalon for three samples, measured with a 26 GHz spectrum analyzer over 1 min.

A detection of a change in the index due to radiation damage can be based on difference of the HF-LF ratio between pre- and post-irradiation. Therefore, all the cavity conditions, including the cavity gain (loss) and cavity alignment, are kept constant over the course of measurement. Initial experiments were made to test the system's consistency. Three $CaF_2$ EPEs were used for these experiments. Their physical thickness, measured based on mechanical measurement, are listed in Table I. Each FPE sample was placed on a mount, which was fixed in the cavity, and the FPE high frequency mode and the laser's repetition rate were recorded using a 26 GHz RF spectrum analyzer and a frequency counter for 1 min. FIG. 4A shows data from one set of the measurement for sample 441, sample 442, and sample 443. Sample 441 has a mean of 16.235409634 GHz and standard deviation of 287.55079 Hz. Sample 442 has a mean of 16.235395378 GHz and standard deviation of 561.60988 Hz. Sample 443 has a mean of 16.23514051 GHz and standard deviation of 384.61657 Hz. After recording the two frequencies with one sample, another FPE sample was replaced without touching cavity optics, and the same measurements are repeated. Data for three samples comprises one data set. This procedure was repeated to make a total of 5 sets. FIG. 4B shows data results for all 5 measurement sets for samples 441, 442, and 443. Over the course of the measurement, there is a systematic shift of the frequency of all three samples.

TABLE I

| Sample # | Thickness (mm) |
|---|---|
| 1 | 6.4727 |
| 2 | 6.4740 |
| 3 | 6.5120 |

Figure 5A:
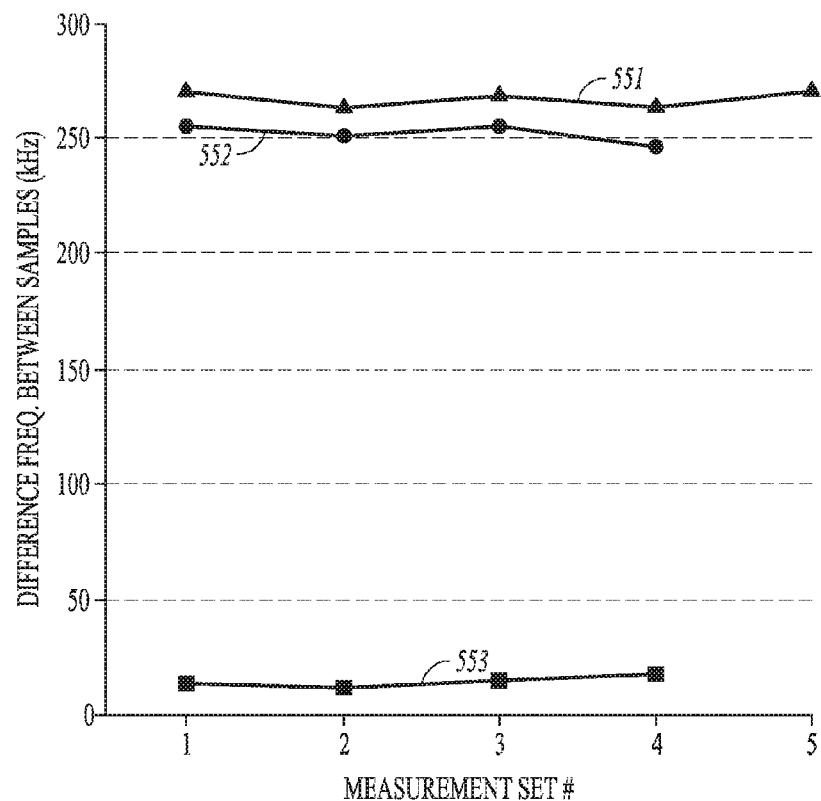
FIG. 5A shows difference of the high frequencies between the samples for each measurement set of FIG. 4B.
Figure 5B:
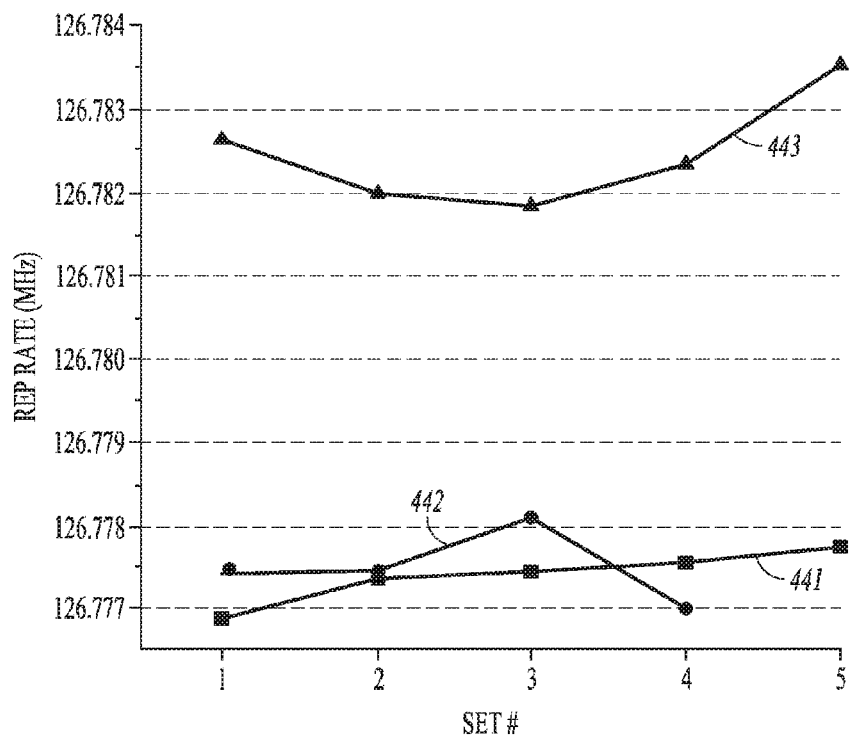
FIG. 5B shows difference of the repetition rate between the samples for each measurement set of FIG. 4B.

Differential measurement is more advantageous because it is less dependent on the cavity misalignment. Difference frequencies were calculated between the FPE high frequency mode for each sample within the same measurement set. For example, the difference frequency between the sample #1 and #3 in the measurement set #1 is $f_{13} \equiv f_1 f_3$. The result is shown in FIG. 5A. Curve 551 is the difference frequency between the sample #1 and #3 at 267.16±3.24 kHz. Curve 552 is the difference frequency between the sample #2 and #3 at 251.99±3.97 kHz. Curve 553 is the difference frequency between the sample #1 and #2 at 14.33±2.67 kHz. The same analysis was performed for the repetition rate, shown in FIG. 5B for samples 441, 442, and 443.

The thickness of sample #3 was different from the other two samples by approximately 0.5% of its thickness. From the high frequency measurement in FIG. 5A, the resolution can be determined as $$R = f_{13}/\Delta f_{13} = (267.16 \text{ kHz})/(3.24 \text{ kHz}) = 82.46 \quad (20)$$

In principle, it should be able to resolve 0.5%/82.5=0.006% change in thickness or equivalently in the index of refraction. For $CaF_2$, with n=1.4305, it should be able to detect a change of $$\Delta n = 0.00006 \times 1.4305 \sim 10^{-4} \quad (21)$$

The width $\Delta f_{ij}$ may be limited by the inaccuracy between the measurement sets. This can be improved by building more stable apparatus. With such stabilization, the ultimate width can be given by the fluctuation of the measurement within a set, which in the current data above is approximately 300 Hz at best. With this value, the resolution improves by a factor of 10.

Figure 6:
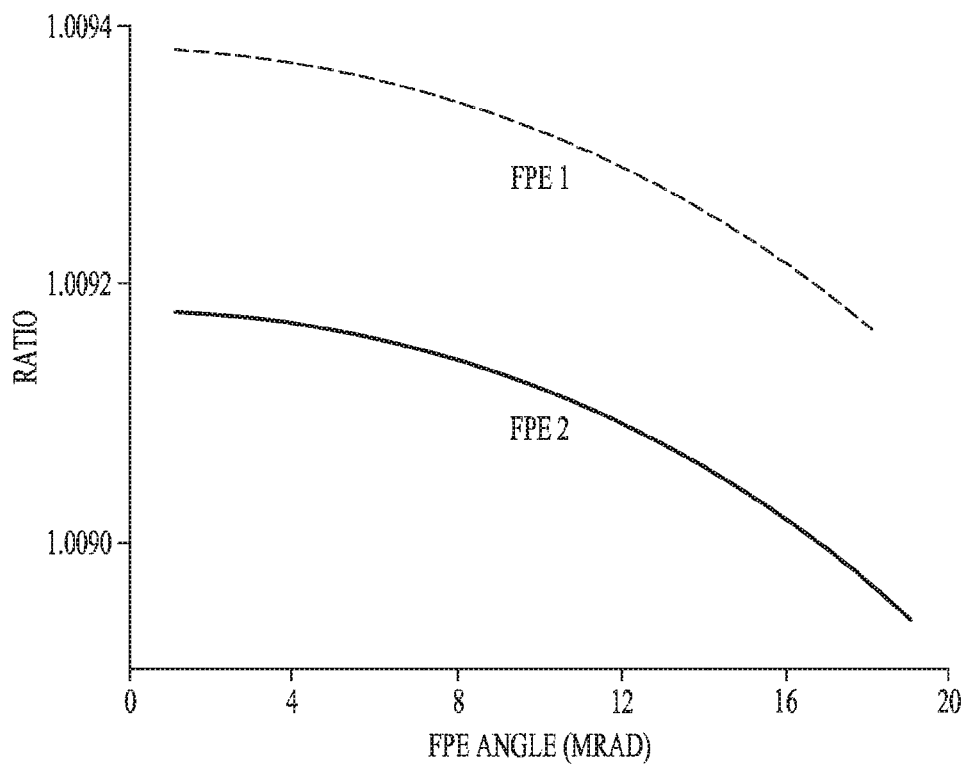
FIG. 6 shows the ratio between the high radio frequency and low radio frequency plotted as a function of the Fabry Perot etalon angle for two different Fabry Perot etalons of the same index but with slightly different thickness.

FIG. 6 shows the ratio between the high radio frequency and low radio frequency plotted as a function of the FPE angle for two different FPEs of the same index but with slightly different thickness. The angular dependence of the ratio is due to the change in the cavity group index (the first term in (6.66)), which is affected by the gain-loss balance. What is remarkable in this measurement is that the two curves are nearly parallel. It means that the angular dependence of the gain-loss balance has not been changed between the two measurements. Only change made between the two measurements are the thickness of the FPEs. The remarkable performance of this method implies that the sensitivity can be further improved by two orders of magnitude ($\Delta n \sim 10^{-6}$).

In various embodiments, measurements of a material can include the generation of an interwoven frequency comb from a nested-cavity mode-locked laser. The interwoven frequency comb is composed of two frequency combs with different mode spacing, with the low frequency from the repetition rate of the laser cavity and the high frequency from the mini-pulse train generated due to an intracavity FPE. The properties of the new class of mode-locked laser, including the frequency tunability, dependence of the comb spacing on the gain and loss, the intricate coupling between the low and high frequencies due to a coupled-cavity resonance condition, are scrutinized. An exploitation of the relation between the high and low frequencies through the cavity resonance can be exploited to measure characteristics of a material. A non-limiting example of such a measurement is the measurement of the index of refraction of a sample arranged as a FPE. Application can be made to measure a small change in the index of refraction of the sample due to stimulus applied to the sample. Structural damage in a crystal by a nuclear radiation, as a stimulus, can be characterized by a nested comb.

From FIG. 1, Fabry-Perot transmission with the Fabry-Perot structure inserted in the laser cavity of a mode-locked laser can provide for generation of a nested comb having multiple combs. See, for example, U.S. Patent Application Ser. No. 61/902,063, filed 22 Jan. 2013, which application is incorporated herein by reference in its entirety. The Fabry-Perot transmission parameters include Fabry-Perot thickness, d, group index, $n_g$, phase index, $n_p$, field transmission function, $\tilde{T}$, a round-trip phase shift, $\delta$, and a round-trip group delay, $\tau_{FP}$, given by:

$$\tilde{T} = \frac{(1-R)e^{i\delta/2}}{1-Re^{i\delta}} \quad (22)$$

$$\delta = \frac{4\pi n_p d \cos\theta_{in}}{\lambda} \quad (23)$$

$$\tau_{FP} = \frac{2n_g d \cos\theta_{in}}{c}. \quad (24)$$

Figure 7:
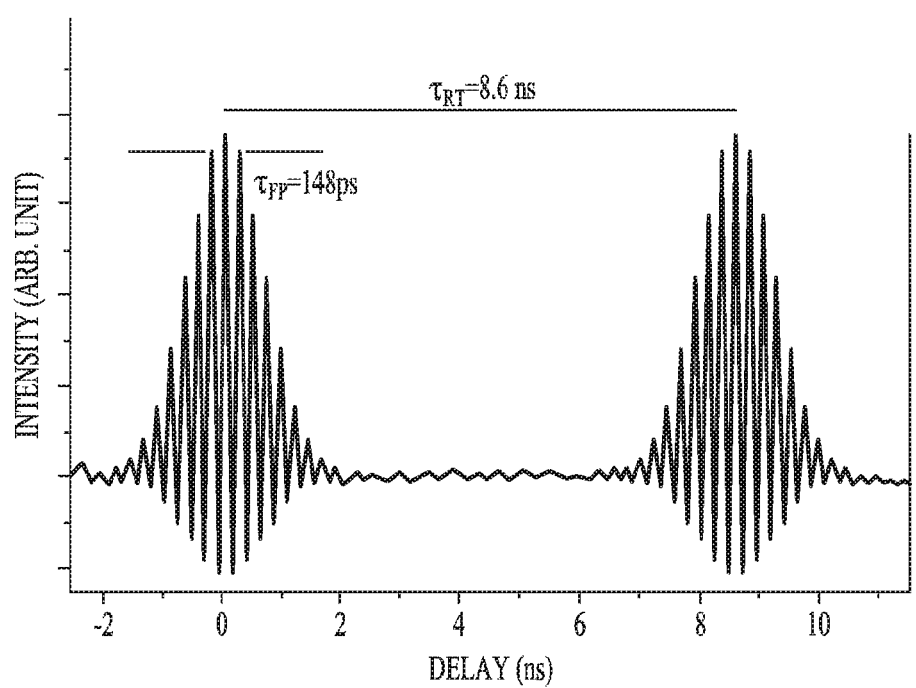
FIG. 7 shows an example of a round-trip group delay of a Fabry Perot structure with respect to group delay of the laser cavity in which the Fabry Perot structure is disposed.
Figure 8:
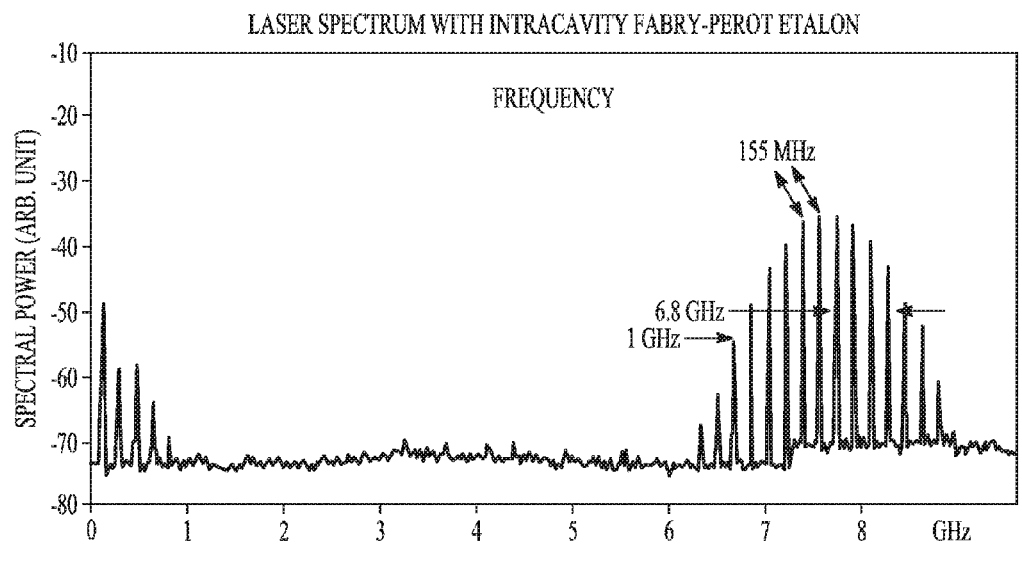
FIG. 8 shows an example of a spectrum associated with a Fabry Perot etalon in a mode-locked laser cavity.
Figure 9:
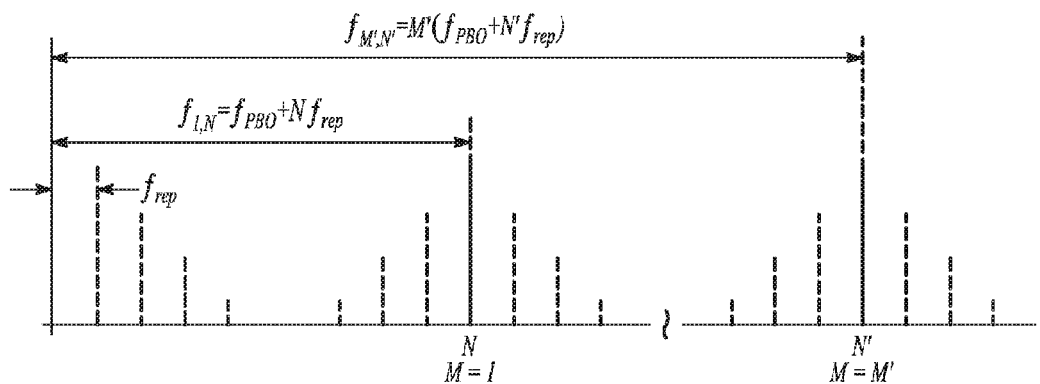
FIG. 9 shows an example of a relationship for frequency related to the frequency associated with the Fabry Perot structure and the frequency of the repetition rate of the mode-locked laser cavity in which the Fabry Perot structure is inserted.

FIG. 7 shows an example of a round-trip group delay, $\tau_{FP}$, of a Fabry Perot structure with respect to group delay $\tau_{RT}$ of the laser cavity in which the Fabry Perot structure is disposed. FIG. 8 shows an example of a spectrum associated with a FPE in a mode-locked laser cavity, where the output of the laser can consist of bursts of a number of pulses at around 6.8 GHz, repeating at the cavity round-trip frequency of 155 MHz. FIG. 9 shows an example of a relationship for frequency related to the frequency associated with the Fabry Perot structure and the frequency of the repetition rate of the mode-locked laser cavity in which the Fabry Perot structure is inserted. This relationship is given by $$V_{mn} = nv_{FP} + mv_{rep}. \quad (25)$$

Figure 10A:
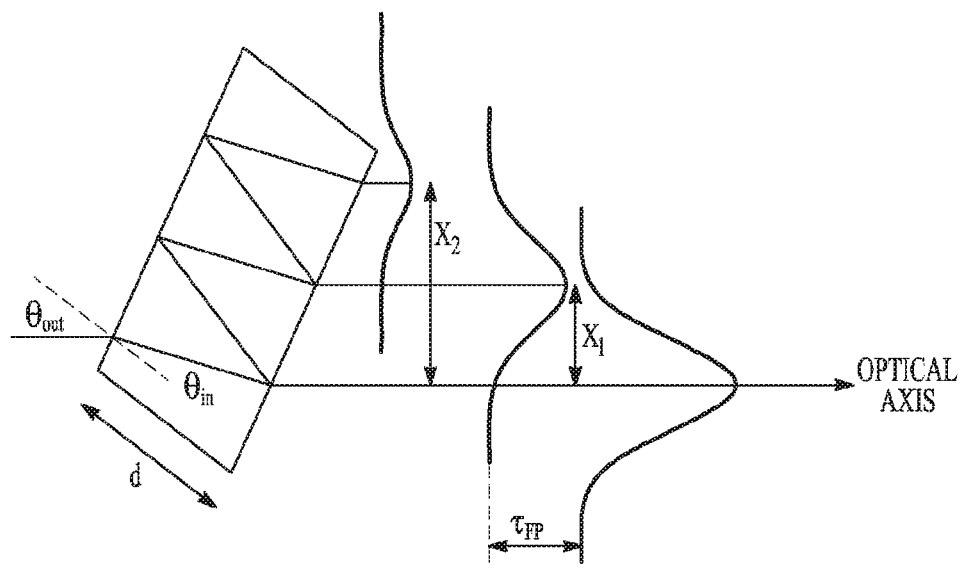
FIG. 10A shows a number of pulses with peak amplitudes at different distances from the optical axis.
Figure 10B:
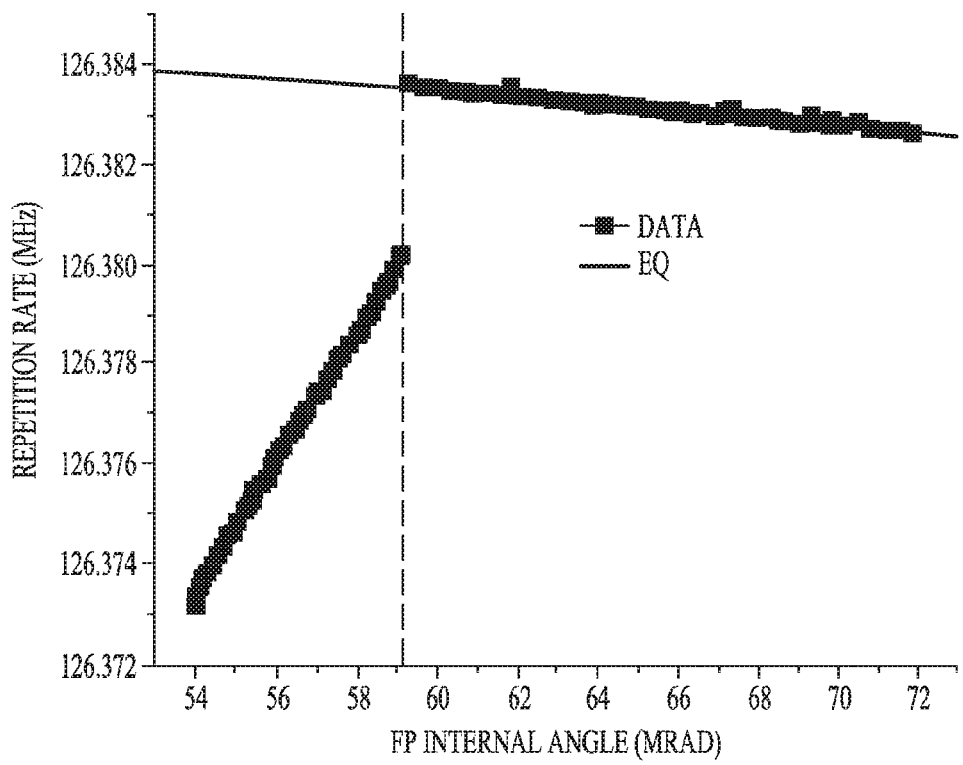
FIG. 10B shows repetition rate of the laser as a function of the internal angle of a Fabry Perot etalon.

As previously noted, the FPE inserted in a laser cavity of a mode-locked laser can produce a symmetric bunch of pulses. The number of pulses in the bunch depends on number of pulses that can interfere. At each round trip of a signal in the laser cavity, a bunch of pulses can be formed by interferences, providing multiple combs, based on the length of the laser cavity, thickness of the Fabry-Perot etalon, and the beam size of the laser in the laser cavity. FIG. 10A shows a number of pulses with peak amplitudes at different distances 0, $x_1$, and $x_2$ from the optical axis. FIG. 10B shows repetition rate of the laser as a function of the internal angle of the FPE.

Figure 11:
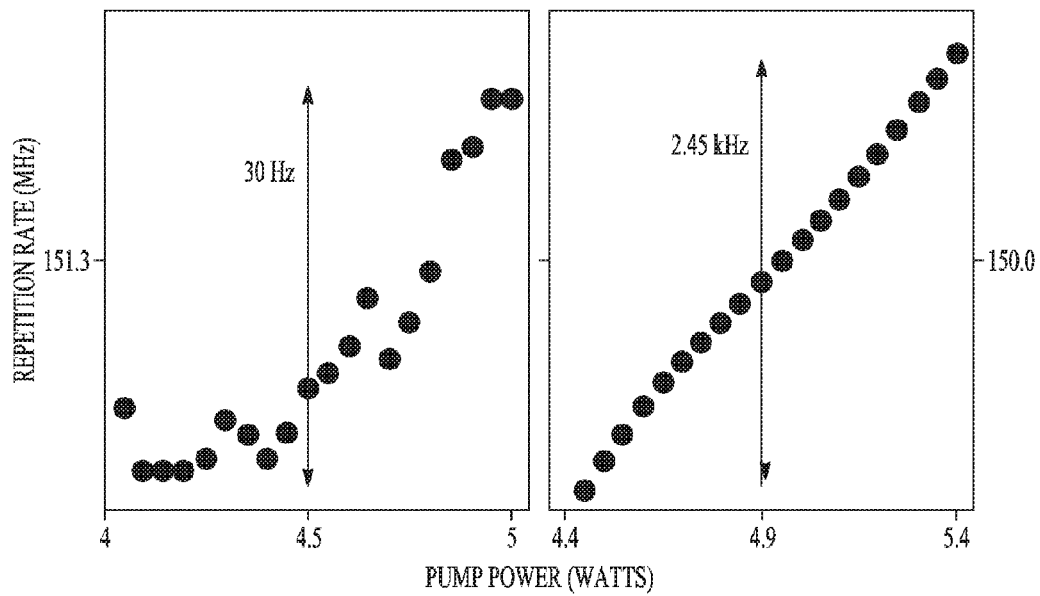
FIG. 11 shows the effect of the pump on the repetition rate.

FIG. 11 shows the effect of the pump on the repetition rate. The effect of the pump on pulse period for a mode-locked laser cavity is shown on the left plot of FIG. 11. The effect of the pump on pulse period for a mode-locked laser cavity with the nested comb is shown in the left plot of FIG. 11.

Figure 12:
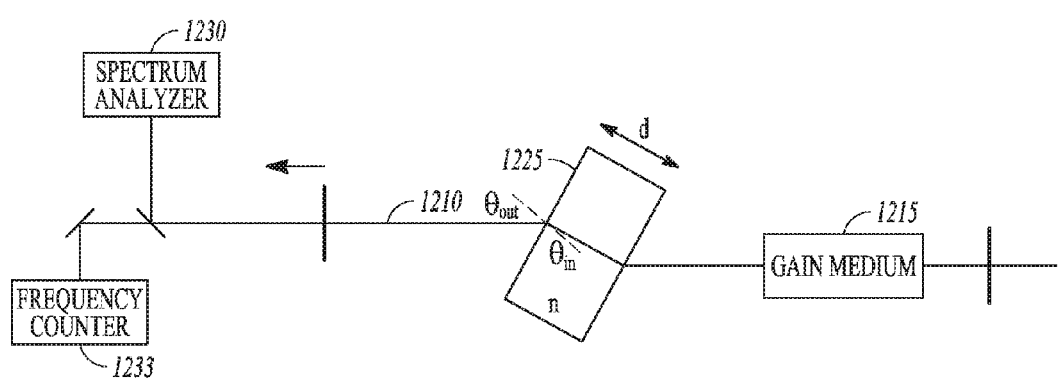
FIG. 12 shows a measurement arrangement including a laser cavity of a mode-locked laser having a gain medium and a Fabry Perot etalon mounted in the laser cavity.
Figure 13A:
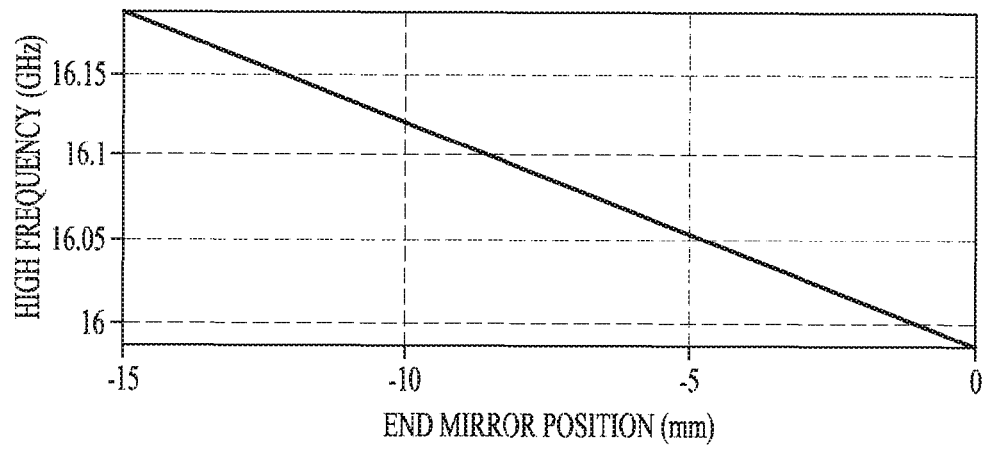
FIG. 13A shows a relationship of the high frequency component of the nested comb to the end mirror position for the arrangement of FIG. 12.
Figure 13B:
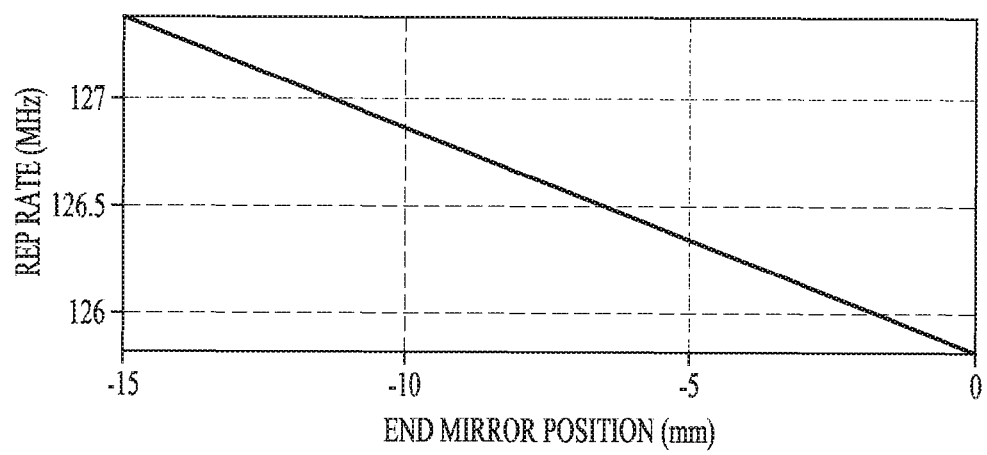
FIG. 13B shows a relationship of the repetition rate to the end mirror position for the arrangement of FIG. 12.

FIG. 12 shows a measurement arrangement including a laser cavity 1210 of a mode-locked laser having a gain medium and a FPE 1225 mounted in the laser cavity 1210. The measurement arrangement includes a spectrum analyzer 1230 and a frequency counter 1233. The HE 1225 can be inserted in the laser cavity 1210 via a mount that provides control of the orientation of the FPE 1225 in the optical path of the laser. The arrangement of the mount may allow for a stimulus to be applied to the FPE 1225 for characterization of the FPE 1225 and/or the stimulus. FIG. 13A shows a relationship of the high frequency component of the nested comb to the end mirror position for the arrangement of FIG. 12. FIG. 13B shows a relationship of the repetition rate to the end mirror position for the arrangement of FIG. 12. The end mirror positioning can be used to provide high and low RF tuning.

Figure 14:
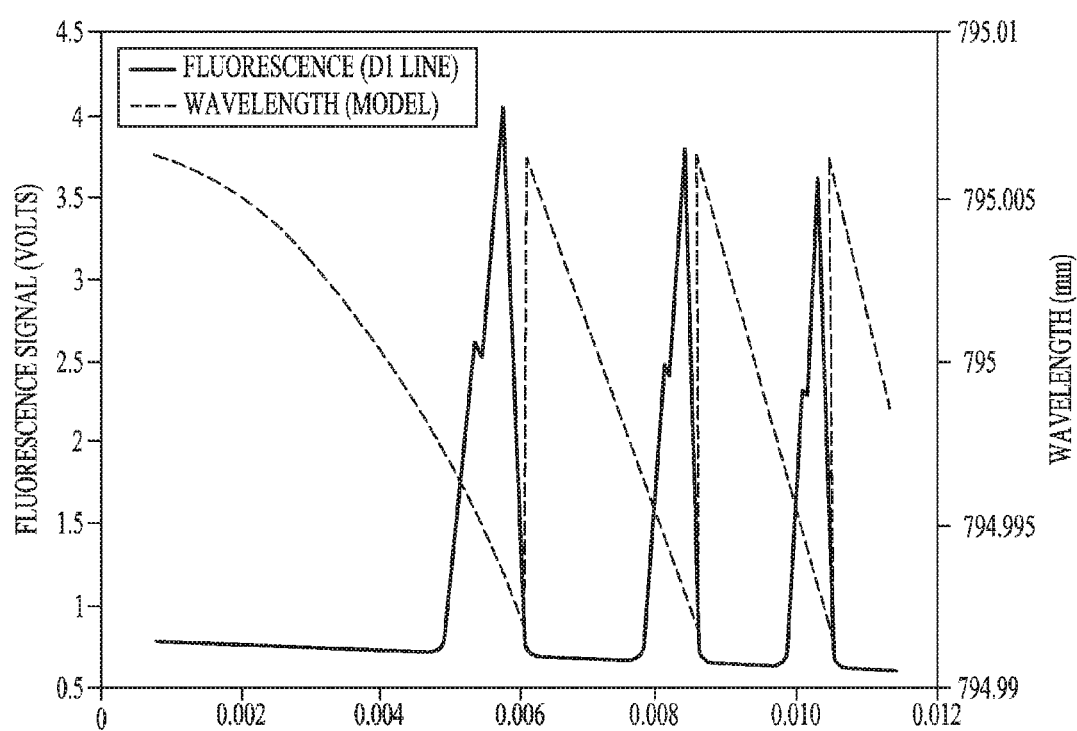
FIG. 14 shows a wavelength model associated with optical frequency tuning of the arrangement of FIG. 12.
Figure 15:
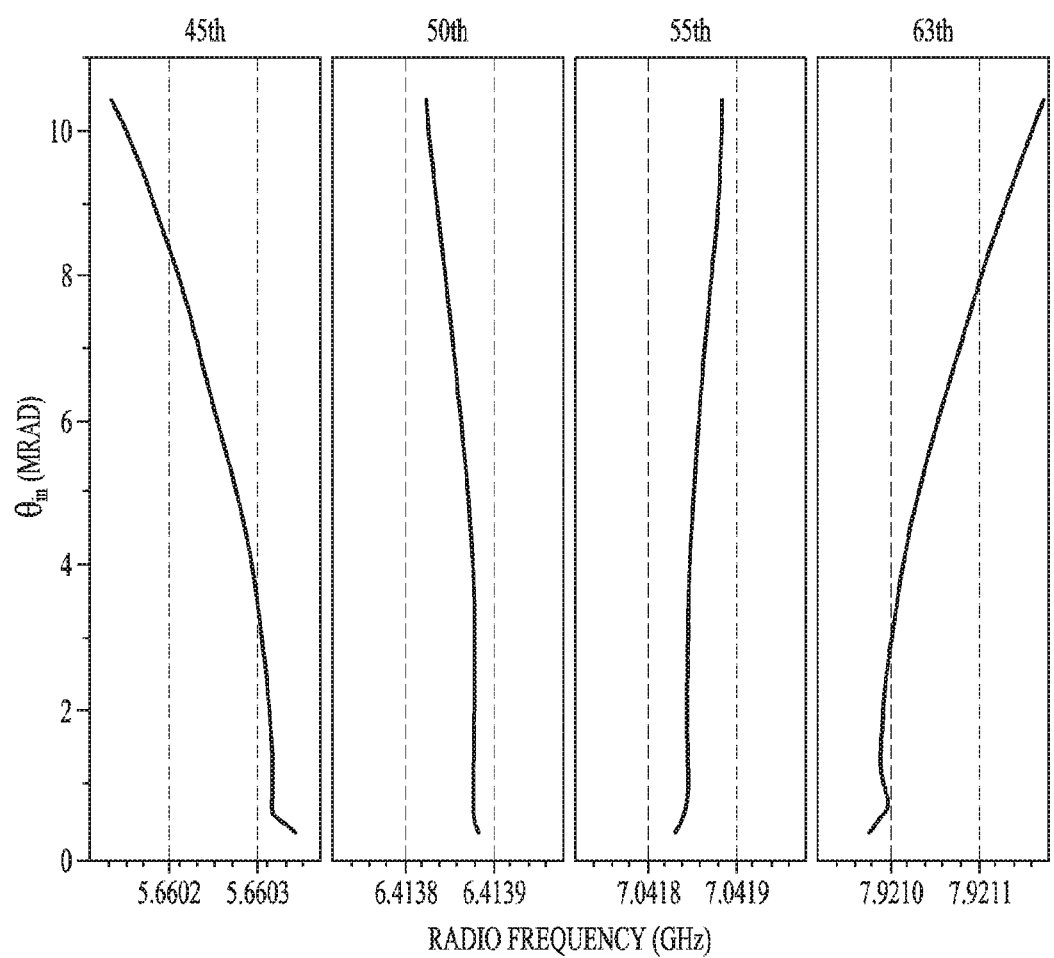
FIG. 15 shows a relationship of internal Fabry Perot etalon angle and radio frequency for the high frequency component of the nested comb.
Figure 16:
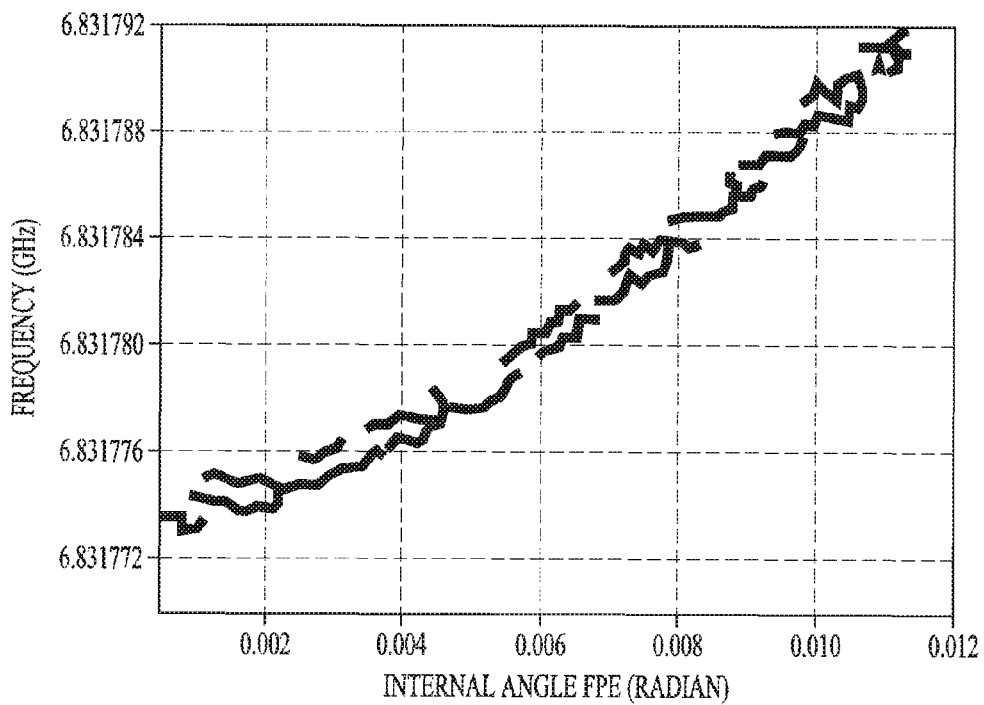
FIG. 16 shows frequency as a function of the internal angle of the Fabry Perot etalon for the high frequency part corresponding to the wide spacing comb in frequency domain.
Figure 17:
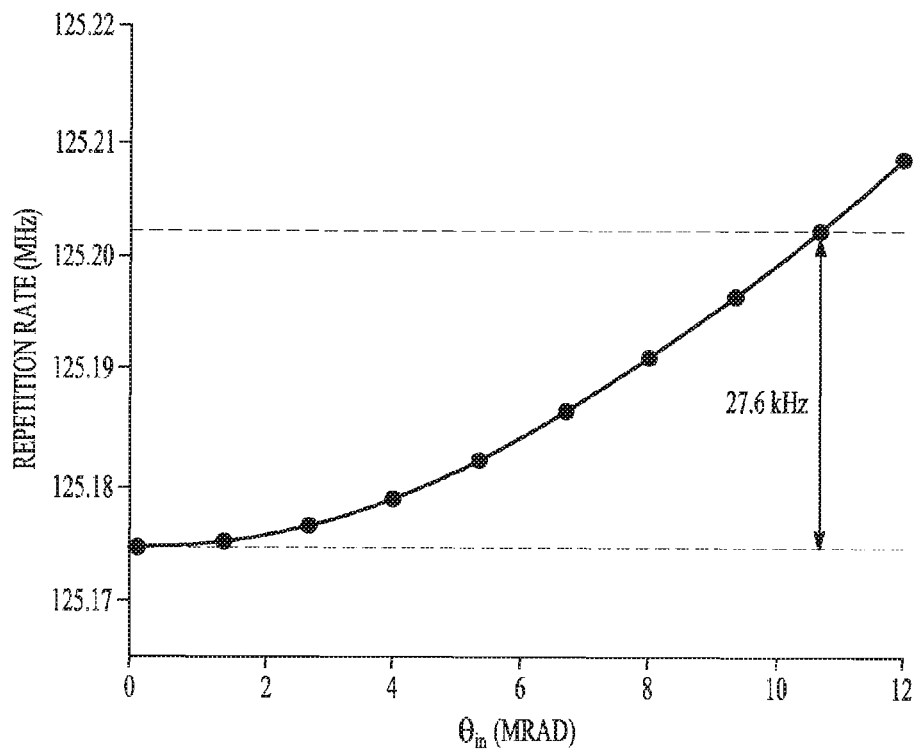
FIG. 17 shows the repetition rate as a function of the internal Fabry Perot etalon angle for the low RF frequency.
Figure 18:
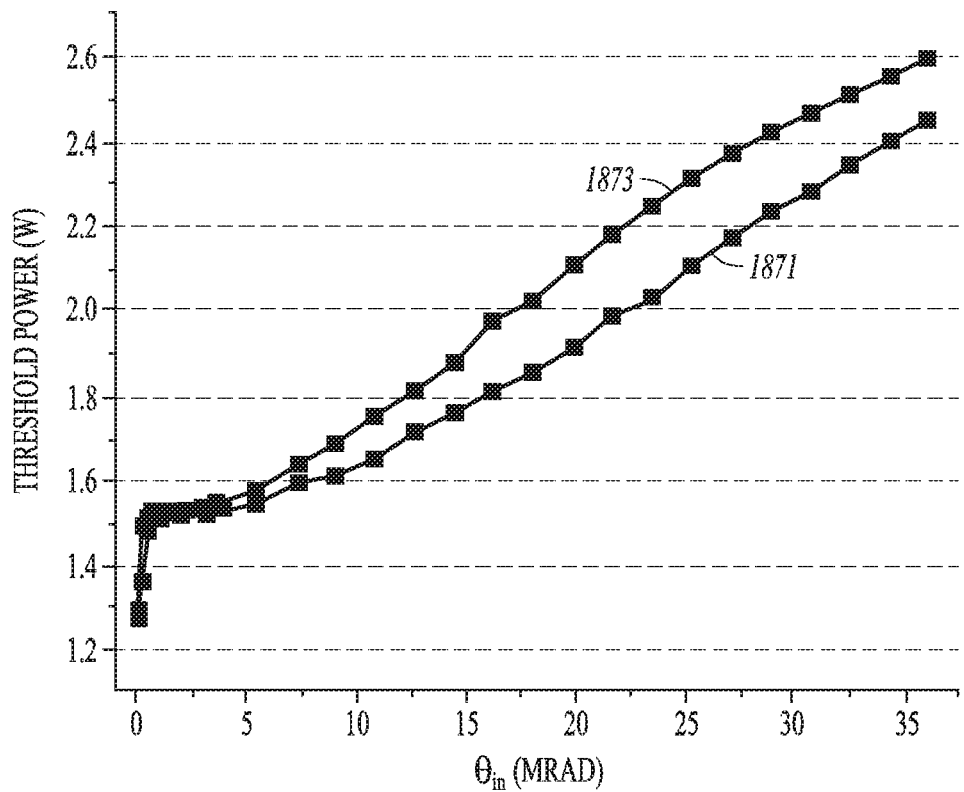
FIG. 18 shows threshold power as a function of the internal Fabry Perot etalon angle for two Fabry Perot etalons of different thickness.

FIG. 14 shows a wavelength model associated with optical frequency tuning of the arrangement of FIG. 12. FIG. 15 shows a relationship of internal FPE angle and radio frequency for the high RF frequency component of the nested comb. The indications 45th, 50th, 55th, and 63th refer to the division of the high frequency by the low frequency (integer part of that division). FIG. 16 shows frequency as a function of the internal angle of the FPE for the high frequency part corresponding to the wide spacing comb in frequency domain. FIG. 17 shows the repetition rate as a function of the internal FPE angle for the low RF frequency. FIG. 18 shows threshold power as a function of the internal FPE angle for two FPEs of different thickness, curve 1871 for a FPE of thickness of 10 mm and curve 1873 for a FPE of thickness of 15 mm.

Figure 19:
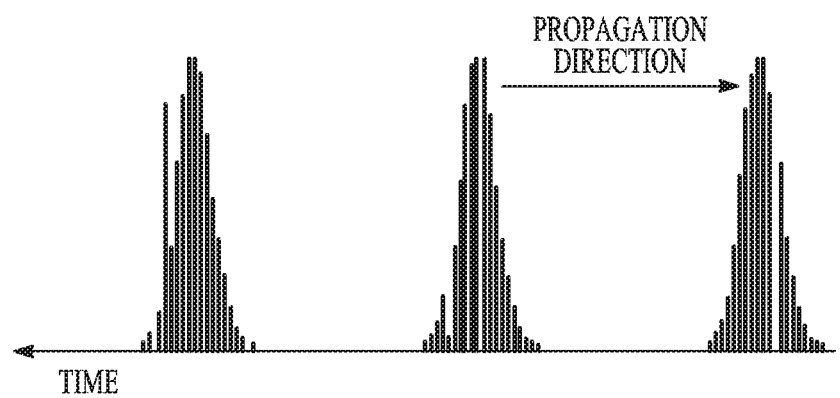
FIG. 19 is a presentation of the propagation of a bunch.
Figure 20:
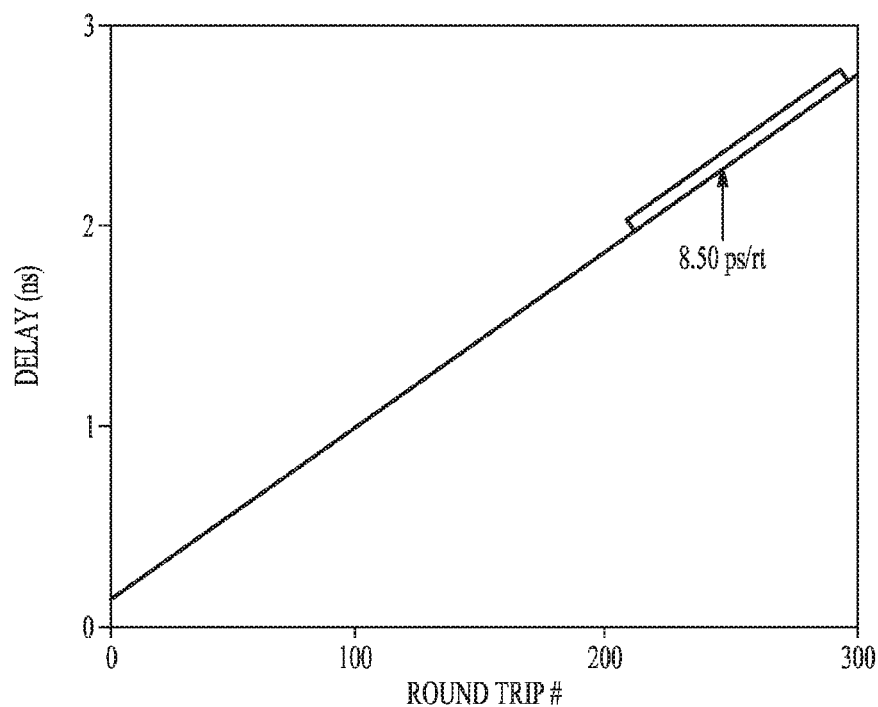
FIG. 20 shows delay as a function of round trip number.

In simulation of the generation of a nested comb, it is noted that there are two competing effects on the laser that result in the formation of a bunch. First, transfer of energy from one pulse to the next in Fabry-Perot delays the pulse bunch in the propagation direction. Second, due to saturation of the gain, the leading pulses in a hunch are amplified more, which advances the pulse hunch in the propagation direction. FIG. 19 is a presentation of the propagation of the bunch. FIG. 20 shows delay as a function of round trip number. Insertion of the Fabry-Perot reduces the pulse period 20 percent more than delay expected in the Fabry-Perot.

A nested comb can be used to determine the change of refractive index of a sample due to stimulus applied to the sample. For instance, application of a nested comb can be used to analyze the change of refractive index of a FPE in the laser cavity due to radiation of the FPE. The central optical frequency is resonant with both cavities:

$$\frac{2\omega_0 L n_{p-c}}{c} = 2N_c\pi \text{ and} \tag{26}$$

$$\frac{2\omega_0 d n_{p-FP}\cos\theta}{c} = 2N_{FP}\pi. \tag{27}$$

The high frequency is defined with a group index as $$v_{fp} = \frac{c}{2dn_{g-fp}\cos\theta}. \tag{28}$$

The cavity pulse round-trip frequency is given by $$v_{rt} = \frac{c}{2Ln_{g-c}}. \tag{29}$$

The optical frequency $\omega_0$ for the nested comb must be resonant simultaneously with Fabry-Perot structure and the laser cavity providing $$\frac{v_{RT}}{v_{FP}} \frac{n_{g-FP} n_{p-c}}{n_{pc} n_{p-FP}} = \frac{N_c}{N_{FP}}. \tag{30}$$

The optical frequency $\omega_l$ must be resonant simultaneously with Fabry Perot and laser cavity:

$$\frac{2\omega_l L n_{pL}}{c} = 2\pi N_L$$
$$\frac{2\omega_l d n_{pFP}}{c} = 2\pi N_{FP} \rightarrow \frac{L}{d} = \frac{N_L}{N_{FP}} \frac{n_p FP}{n_{pL}} \tag{31}$$

$$\boxed{\frac{HF}{LF} = f_{FP} \times \tau_{rt} = \frac{2L}{c}n_{gL} \div \frac{2d}{c}n_{gFP} = \frac{n_{gL}}{n_{gFP}} \frac{N_L}{N_{FP}}}$$

All other conditions being equal, the ratio HF/LF measures the phase index of refraction of the FPE, $n_{pFP}$. Measuring this ratio before and after irradiation of the FPE allows for determination of the change of refraction due to radiation. Other stimuli applied to the FPE can be analyzed in a similar manner.

Figure 21:
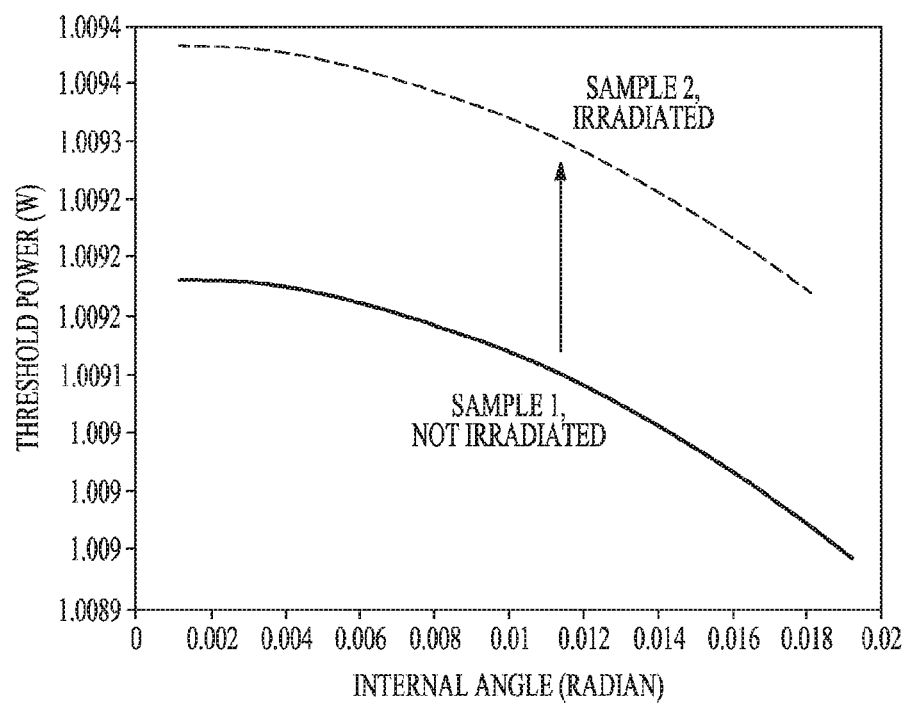
FIG. 21 shows the ratio of high frequency to low frequency as a function of internal angle of a Fabry Perot etalon for two scenarios.

FIG. 21 shows the ratio of high frequency to low frequency as a function of internal angle of the FPE for two scenarios. Sample 1 is for a material structured as a FPE that is not irradiated. Sample 2 is for the material structured as a FPE that is irradiated. At a selected internal angle, the ratio of the index of refraction of the FPE irradiated to the index of refraction of the FPE not irradiated is $$\frac{(n_{p-fp})_2}{(n_{p-fp})_1} = 1.00000279 \text{ with standard deviation of } 3e-8. \tag{32}$$

Figure 22:
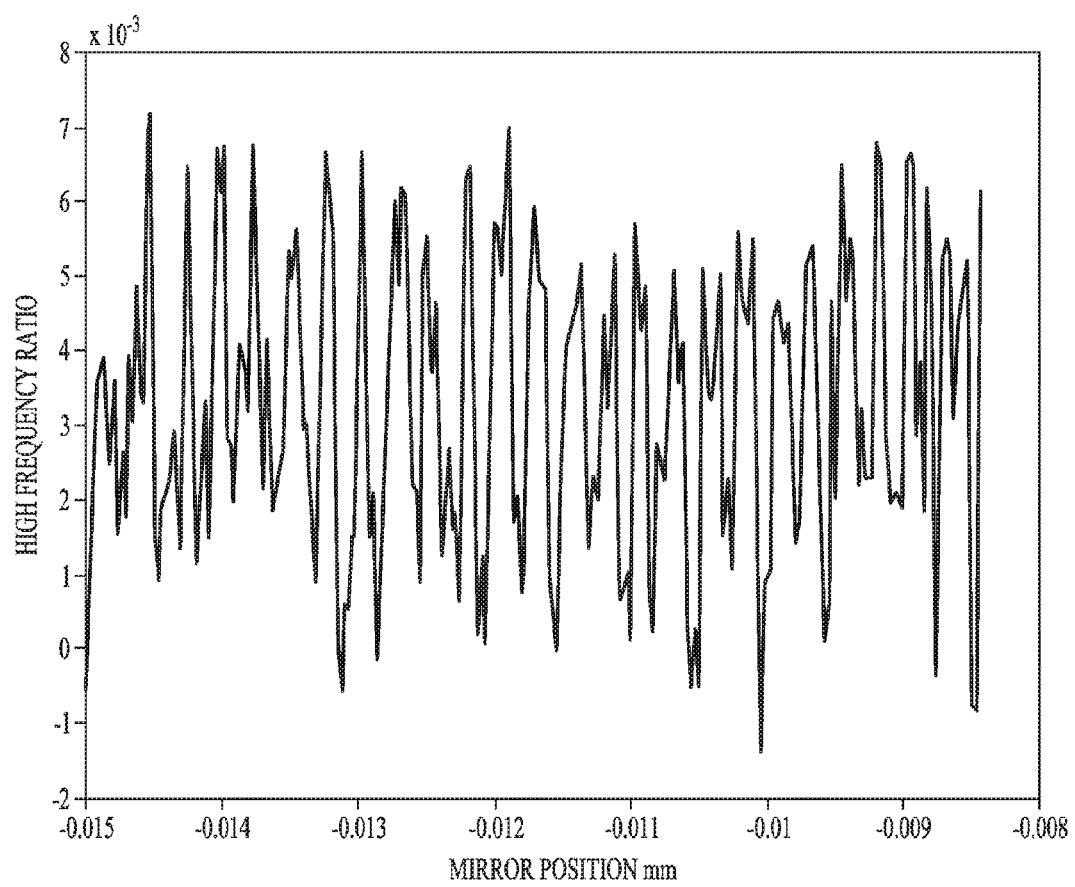
FIG. 22 shows high frequency ratio as a function of mirror position providing an indication of resolution.

FIG. 22 shows high frequency ratio as a function of mirror position providing an indication of resolution.

Figure 23:
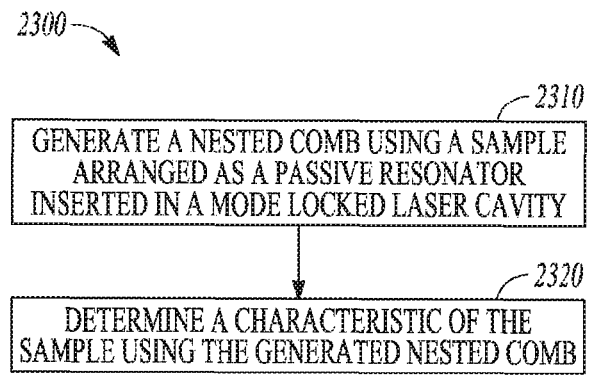
FIG. 23 is a flow diagram of features of an example method to characterize a sample.

FIG. 23 is a flow diagram of features of an example embodiment of a method 2300 to characterize a sample. At 2310, a nested comb is generated using a sample arranged as a passive resonator inserted in a mode-locked laser cavity. The nested comb has multiple frequency combs. The sample can be arranged as a FPE. At 2320, a characteristic of the sample is determined using the generated nested comb. The characteristic can include an index of refraction of the sample. The mode-locked laser cavity has a cavity length and the sample can be arranged as a Fabry Perot etalon, where method 2300 or a similar method can include measuring phase and group index of the mode-locked laser cavity and the Fabry Perot etalon based on a resonant condition coupling the multiple frequency combs.

Method 2300 or a similar method can include applying a stimulus to the sample; and determining a change in the characteristic of the sample based on a change of the multiple frequency combs in response to the stimulus applied to the sample. The change in the characteristic of the sample can include a change in the index of refraction of the sample. The mode-locked laser cavity has a cavity length and the sample can be arranged as a Fabry Perot etalon, where method 2300 or a similar method can include scanning the cavity length and angle tuning the etalon, providing higher precision to measurement of the index of refraction. Applying the stimulus to the sample can include irradiating the sample. Method 2300 or a similar method can include characterizing material of the sample as a function of parameters correlated to irradiating the sample. Method 2300 or a similar method can include generating a characterization of a source irradiating the sample. Irradiating the sample can include irradiating the sample with neutrons, gamma rays, or neutrons and gamma rays. Method 2300 or a similar method can include determining the index of refraction of the sample as a function of irradiating the sample with neutrons.

Method 2300 or a similar method can include generating a nested comb using another sample arranged as a passive resonator inserted in a mode-locked laser cavity to generate multiple frequency combs, the other sample providing a reference. Crystals can be used as the sample and the other sample. Features discussed with respect to any of FIGS. 1-24 or combinations of features, as taught herein, may be appropriately combined into a method that uses a nested frequency comb according to the teachings herein.

Figure 24:
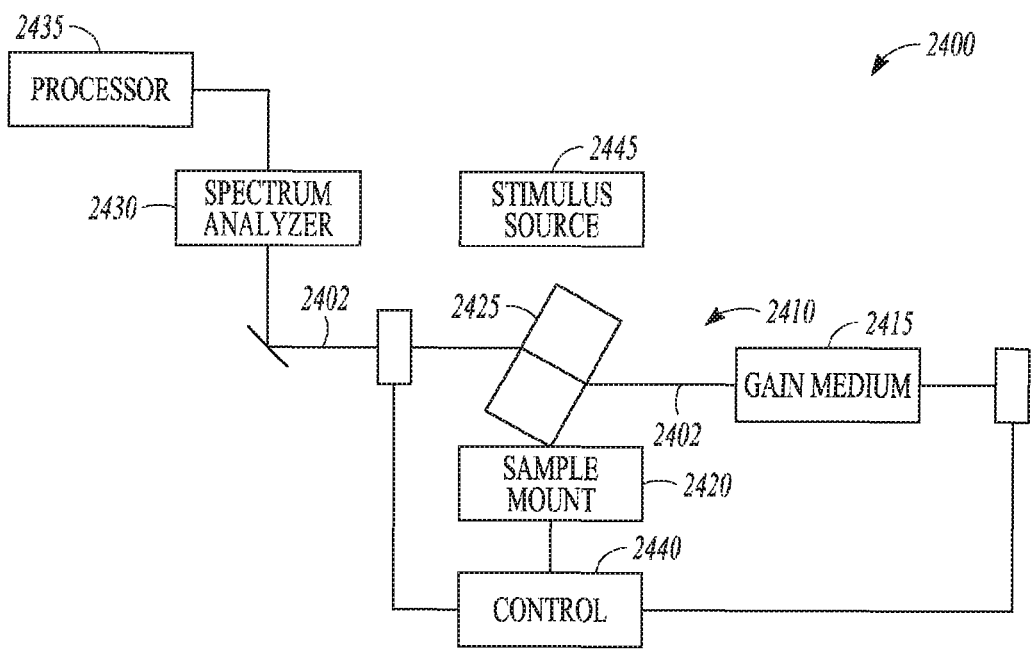
FIG. 24 is a schematic of an example system structured to characterize a sample, a source that stimulates the sample, or both a sample and a source that stimulates the sample.

FIG. 24 is a schematic of an embodiment of an example system 2400 structured to characterize a sample, a source that stimulates the sample, or both a sample and a source that stimulates the sample. System 2400 comprises a mode-locked laser 2405 having a laser cavity 2410, referred to as a mode-locked laser cavity 2410, a gain medium 2415, and a sample mount 2420 disposed in mode-locked laser cavity 2410. System 2400 can also comprise a spectrum analyzer 2430 and a processor 2435. Sample mount 2420 can be disposed in mode-locked laser cavity 2410 such that a sample 2425 arranged as a passive resonator inserted in mode-locked laser cavity 2410 via sample mount 2420 is operable in conjunction with a laser beam of mode-locked laser cavity 2410 along propagation path 2402 to generate a nested comb having multiple frequency combs. The spectrum analyzer 2430 can be disposed to operably receive the multiple frequency combs. Processor 2435 can be coupled to spectrum analyzer 2430 to operatively determine a characteristic of sample 2425 based on the multiple frequency combs operably received by spectrum analyzer 2430.

System 2400 or a similar system can include mode-locked laser cavity 2410 structured with an access path arranged such that a stimulus is operably applied to sample 2445; and processor 2435 is operable to determine a change in the characteristic of sample 2425 based on a change of the multiple frequency combs in response to the stimulus applied to sample 2425. The characteristic can be an index of refraction of sample 2425. System 2400 or a similar system can include a control 2440 to scan the cavity length and angle tune sample 2425 when arranged as a Fabry Perot etalon, to provide higher precision to measurement of the index of refraction. Scanning the cavity length can include adjusting the cavity length.

System 2400 or a similar system can include an irradiating source 2445 to apply the stimulus to sample 2425. System 2400 or a similar system can include processor 435 operable to characterize material of sample 2425 as a function of parameters correlated to irradiating source 2445. Irradiating source 2445 can include a neutron source, a gamma ray source, both a neutron source and a gamma ray source, or other stimulating source operable to stimulate 2425 without modifying other components of the mode-locked laser 2405.

System 2400 or a similar system can include the sample mount 2420 structured to operably exchange samples into the mode-locked laser cavity 2419, where each sample is arranged as a passive resonator inserted in a mode-locked laser cavity to generate multiple frequency combs. The samples as passive resonators can be structured as FPEs. Features discussed with respect to any of FIGS. 1-23 or combinations of features, as taught herein, may be appropriately combined into a system according to the teachings herein.

Although specific embodiments have been illustrated and described herein, it will be appreciated by those of ordinary skill in the art that any arrangement that is calculated to achieve the same purpose may be substituted for the specific embodiments shown. Upon studying the disclosure, it will be apparent to those skilled in the art that various modifications and variations can be made in the devices and methods of various embodiments of the invention. Various embodiments can use permutations and/or combinations of embodiments described herein. Other embodiments will be apparent to those skilled in the art from consideration of the specification and practice of the embodiments disclosed herein. It is to be understood that the above description is intended to be illustrative, and not restrictive, and that the phraseology or terminology employed herein is for the purpose of description.

What is claimed is:

1. A system comprising:
   a mode-locked laser cavity having a cavity length;
   a sample mount disposed in the mode-locked laser cavity such that a sample arranged as a passive resonator inserted in the mode-locked laser cavity via the sample mount is operable in conjunction with a laser beam of the mode-locked laser cavity to generate a nested comb having multiple frequency combs; and
   a spectrum analyzer disposed to operably receive the multiple frequency combs; and
   a processor coupled to the spectrum analyzer to operatively determine a characteristic of the sample based on the multiple frequency combs operably received by the spectrum analyzer.

2. The system of claim 1, wherein the mode-locked laser cavity is structured with an access path arranged such that a stimulus is operably applied to the sample; and the processor is operable to determine a change in the characteristic of the sample based on a change of the multiple frequency combs in response to the stimulus applied to the sample.

3. The system of claim 2, wherein the characteristic is an index of refraction of the sample.

4. The system of claim 3, wherein the system includes a control to scan the cavity length and angle tune the sample when arranged as a Fabry Perot etalon, to provide higher precision to measurement of the index of refraction.

5. The system of claim 2, wherein the system includes an irradiating source to apply the stimulus to the sample.

6. The system of claim 5, wherein the processor is operable to characterize material of the sample as a function of parameters correlated to irradiating source.

7. The system of claim 5, wherein the irradiating source includes a neutron source, a gamma ray source, or both a neutron source and a gamma ray source.

8. The system of claim 1, wherein the sample mount to exchange samples into the mode-locked laser cavity, each sample arranged as a passive resonator inserted in a mode-locked laser cavity to generate multiple frequency combs.

* * * * *